United States Patent [19]

Gerecke et al.

[11] 4,006,144
[45] Feb. 1, 1977

[54] 10,11-DIHYDRO-DIBENZO(b,f)THIEPIN DERIVATIVES

[75] Inventors: Max Gerecke, Reinach; Jean-Pierre Kaplan, Bubendorf; Emilio Kyburz, Reinach, all of Switzerland

[73] Assignee: Hoffmann-La Roche Inc., Nutley, N.J.

[22] Filed: Oct. 3, 1975

[21] Appl. No.: 619,149

Related U.S. Application Data

[62] Division of Ser. No. 378,730, July 12, 1973, Pat. No. 3,929,791.

[30] Foreign Application Priority Data

July 21, 1972   Switzerland ............ 1001/72
May 17, 1973   Switzerland ............ 7059/73

[52] U.S. Cl. .................. 260/268 TR; 260/244 R; 260/256.4 C; 260/256.5 R; 260/268 H; 424/250
[51] Int. Cl.$^2$ ........................ C07D 409/14
[58] Field of Search ............ 260/268 TR

[56] References Cited

UNITED STATES PATENTS

| | | | |
|---|---|---|---|
| 3,646,037 | 2/1972 | Schindler et al. | 260/268 TR |
| 3,646,039 | 2/1972 | Schindler et al. | 260/268 TR |
| 3,699,107 | 10/1972 | Schindler et al. | 260/268 TR |
| 3,725,409 | 4/1973 | Protiva et al. | 260/268 TR |
| 3,828,046 | 8/1974 | Doerhoffer | 260/268 TR |
| 3,929,791 | 12/1975 | Gerecke et al. | 260/268 TR |

OTHER PUBLICATIONS

Gosteli, Jacques Chemical Abstracts vol. 77, p. 114,271j, (1972).

*Primary Examiner*—Donald G. Daus
*Assistant Examiner*—Jose Tovar
*Attorney, Agent, or Firm*—Samuel L. Welt; Bernard S. Leon; William G. Isgro

[57]         ABSTRACT

Dibenzothiepin derivatives of the general formula

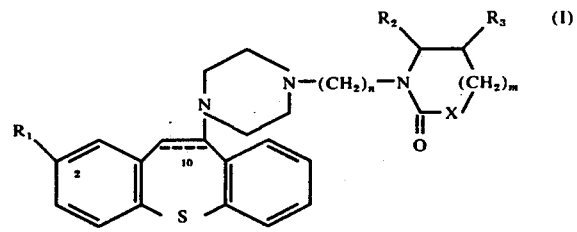

wherein $m$, $n$, $R_1$, $R_2$, $R_3$ and X are as hereinafter set forth, and salts thereof as well as processes for their manufacture are disclosed. The end products are useful as central-depressant and neuroleptic agents.

3 Claims, No Drawings

10,11-DIHYDRO-DIBENZO(b,f)THIEPIN DERIVATIVES

This is a division of application, Ser. No. 378,730, filed July 12, 1973, now U.S. Pat. No. 3,929,791 issued Dec. 30, 1975.

DESCRIPTION OF THE INVENTION

The present invention relates to tricyclic compounds of the general formula

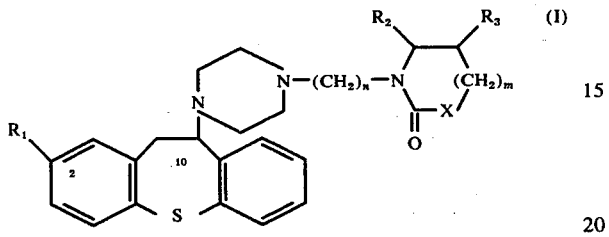

wherein n stands for 2, 3 or 4, $R_1$ represents a halogen atom or a lower alkyl, di(lower alkyl)sulphamoyl, nitro, amino, di(lower alkyl)amino or trifluoromethyl group, X represents an oxygen atom or an imino, (lower alkyl)imino or methylene group, m stands for zero or 1 and $R_2$ and $R_3$ each represent a hydrogen atom or $R_2$ and $R_3$ together represent the grouping

and wherein the bond indicated by a broken line can be hydrogenated, and pharmaceutically acceptable salts thereof.

As used in this description and in the accompanying claims, the term "lower alkyl", alone or in combination with other groups, preferably means aliphatic groups which contain 1 to 6 carbon atoms and which can be branched-chain or straight-chain. Examples of such groups are methyl, ethyl, isopropyl, n-hexyl etc. The term "halogen" means fluorine, chlorine, bromine and iodine, chlorine being preferred.

It was found that the compounds of formula I and their salts exhibit strong central-depressant and neuroleptic properties. They can accordingly be used, for example, for the treatment of acute or chronic schizophrenia and as transquilisers. A particular advantage is that no cataleptic side-effects or only slight cataleptic side-effects occur, so that no motoric disorders or only insignificant motoric disorders are observed. A preferred group of tricyclic compounds of this invention comprises those compounds of formula I in which the bond indicated by a broken line is hydrogenated and salts thereof. 3-[2-[4-(2-chloro-10,11-dihydro-dibenzo[b,f]thiepin-10-yl)-1-piperazinyl]-ethyl]-2-oxazolidinone and 3-[2-[4-(10,11-dihydro-2-methyl-dibenzo[b,f]thiepin-10-yl)-1-piperazinyl]-ethyl]-2-oxazolidinone and their salts are especially preferred.

The tricyclic compounds of formula I and their salts are prepared by:

a. reacting a compound of the general formula

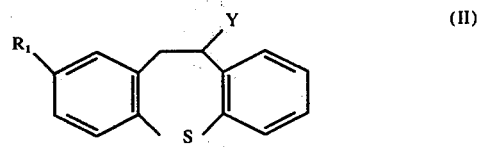

wherein $R_1$ has the significance given earlier and Y represents a leaving atom with a compound of the general formula

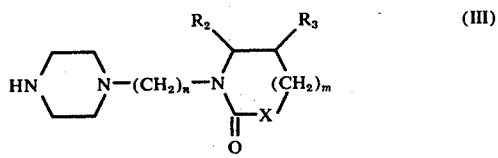

wherein m, n, $R_2$, $R_3$ and X have the significance given earlier, to give a compound of formula I in which the bond indicated by a broken line is hydrogenated, or b. reducing a compound of the general formula

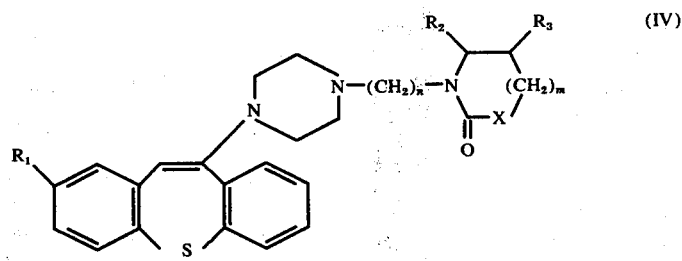

wherein m, n, $R_1$, $R_2$, $R_3$ and X have the significance given earlier, to give a compound of formula I in which the bond indicated by a broken line is hydrogenated, or c. reacting a compound of the general formula

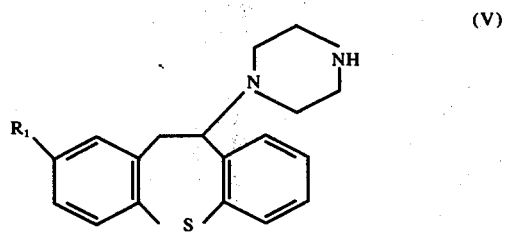

wherein $R_1$ has the significance given earlier, with a compound of the general formula

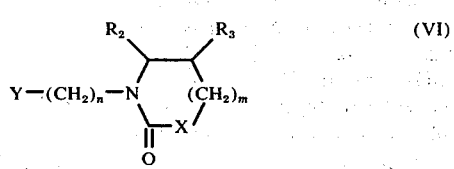

(VI)

wherein $m$, $n$, X, Y, $R_2$ and $R_3$ have the significance given earlier, to give a compound of formula I in which the bond indicated by a broken line is hydrogenated, or d. reacting a compound of the general formula

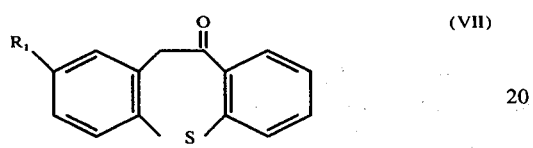

(VII)

wherein $R_1$ has the significance given earlier, with a compound of formula III hereinbefore to give a compound of formula I in which the bond indicated by a broken line is not hydrogenated.

After any of steps (a) - (d) above, if desired, a nitro group denoted by $R_1$ can be reduced to the amino group, if desired, an amino group denoted by $R_1$ can be di(lower alkylated) and, if desired, a compound of formula I obtained can be converted into a salt.

The leaving group denoted by Y in the starting materials of formula II is preferably a halogen atom or an alkyl-substituted or aryl-substituted sulphonyloxy group. Alkyl groups or aryl groups present in the leaving group Y are preferably lower groups, especially the methyl group or the phenyl or tolyl group. Halogen atoms present are preferably chlorine or bromine.

The starting materials of formula II are known compounds or analogues of known compounds which can be prepared by known methods. For example, the starting materials of formula II in which Y has various meanings can be prepared as follows:

Y = halogen: These starting materials can be prepared from a corresponding 10-hydroxy compound and a suitable halide (e.g. thionyl chloride or thionyl bromide) or a hydrogen halide in the presence of a water-binding agent (e.g. hydrogen chloride in the presence of calcium chloride).

Y = alkyl-substituted or aryl-substituted sulphonyloxy: These starting materials can be prepared from a corresponding 10-hydroxy compound and an alkyl-substituted or aryl-substituted sulphonic acid halide (e.g. the chloride).

The starting materials of formula III can be prepared, for example, according to the following formula scheme in which $m$, $n$, X, Y, $R_2$ and $R_3$ have the significance given earlier and $R_4$ represents a suitable protecting group such as the benzyl group or a lower alkoxycarbonyl group (e.g. the methoxycarbonyl or ethoxycarbonyl group).

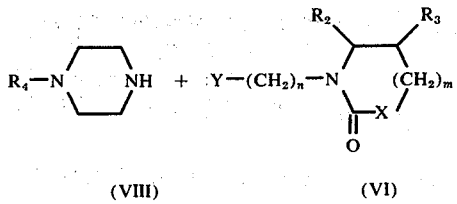

(VIII)  (VI)

↓

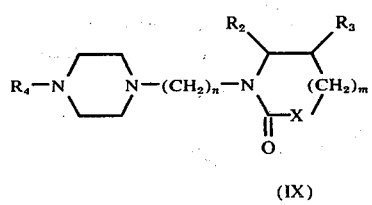

(IX)

↓

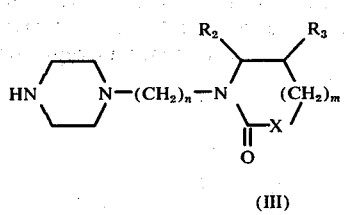

(III)

The condensation of a compound of formula VIII with a compound of formula VI is preferably carried out in the presence of an acid-binding agent (e.g. potassium carbonate or triethylamine). The protecting group denoted by $R_4$ is subsequently removed from the condensation product of formula IX, the benzyl group by hydrogenolysis, the alkoxycarbonyl group e.g. by alkaline hydrolysis, to give a starting material of formula III.

The reaction of a compound of formula II with a compound of formula III in accordance with process embodiment (a) above is expediently carried out in an inert organic solvent; for example, in an aromatic hydrocarbon (e.g. benzene or toluene) a chlorinated hydrocarbon (e.g. methylene chloride, trichloroethylene, chloroform, carbon tetrachloride or chlorobenzene), an aliphatic or cyclic ether (e.g. diethyl ether, tetrahydrofuran or dioxane) or dimethylformamide or dimethyl sulphoxide. The reaction is expediently carried out at a temperature between about 30° C and about 200° C, preferably at a temperature in the region of about 100° C. Where a compound of formula II in which Y represents a halogen atom or an alkyl-substituted or aryl-substituted sulphonyloxy group, the reaction is preferably carried out in the presence of an acid-binding agent, preferably in the presence of an alkali carbonate (e.g. potassium carbonate) or in the presence of an excess of the compound of formula III.

The reduction of an enamine of formula IV in accordance with process embodiment (b) above is preferably carried out by treatment with an alkali metal borohydride in the presence of a strong acid. Sodium borohydride or potassium borohydride, especially sodium borohydride, is preferably used as the alkali metal borohydride. However, lithium borohydride can also be used. The strong acid can be either an organic acid or an inorganic acid. Suitable organic acids are branched-chain or straight-chain, lower mono- or dicarboxylic acids which contain up to 4 carbon atoms and which may be halogen-substituted (e.g. formic acid, acetic acid, trichloroacetic acid, trifluoroacetic acid, propionic acid, isobutyric acid, oxalic acid and the like). Acetic acid is preferred and oxalic acid is especially preferred. Suitable inorganic acids are, in particular, sulphuric acid, hydrohalic acids, especially hydrochloric acid, and the like. A preferred inorganic acid is concentrated sulphuric acid. Since the enamines of formula IV are unstable in the presence of water, the reduction is expediently carried out in the absence of water, there being expediently used only anhydrous acids or only those acids which, if they contain some water, do not release water (e.g. concentrated sulphuric acid). The reduction with an alkali metal borohydride and a strong acid is advantageously carried out in an ether, e.g. diethyl ether, tetrahydrofuran, dioxane, diethyleneglycol dimethyl ether (diglyme) or dimethoxymethane and at a temperature between room temperature and the reflux temperature of the solvent, preferably at the reflux temperature. The reduction of the enamines of formula IV can also be carried out by other methods; for example, by treatment with formic acid or with zinc and glacial acetic acid. These reduction methods are also preferably carried out at a temperature between room temperature and the reflux temperature of the solvent, preferably at the reflux temperature. When the reduction is carried out with zinc and glacial acetic acid, a nitro group denoted by $R_1$ is to a considerable extent reduced to the amino group.

The starting materials of formula V can be prepared, for example, by reacting a compound of formula II with a mono-(N-protected)-piperazine (e.g. N-carbethoxy-piperazine). The reaction product is subsequently subjected to an alkaline saponification (e.g. with the aid of aqueous alkali).

The leaving group present in the starting materials of formula VI is of the same type as in the case of the starting materials of formula II. The starting materials of formula VI can be prepared, for example, by first converting a lactam of the general formula

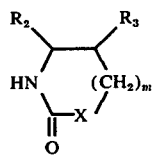 (X)

wherein $m$, X, $R_2$ and $R_3$ have the significance given earlier, into the corresponding alkalli metal salt (e.g. the sodium salt). This conversion can be carried out, for example, by treating a compound of formula X with an alkali metal hydride or alkali metal amide in an aromatic hydrocarbon (e.g. benzene or toluene) or dimethylformamide. The alkali metal salt is then reacted with a compound of the general formula

 (IX)

wherein $n$ has the significance given earlier, Hal represents a halogen atom and $R_5$ represents a suitable protecting group (e.g. the benzyl or 2-tetrahydropyranyl group).

The protecting group denoted by $R_5$ in the reaction product is subsequently cleaved off hydrogenolytically or hydrolytically. The hydroxy compound obtained is reacted with a halogenating agent (e.g. thionyl chloride) or with an alkyl-substituted or aryl-substituted sulphonic acid halide (e.g. the chloride) to give the desired starting material of formula VI.

The reaction of a compound of formula V with a compound of formula VI in accordance with process embodiment (c) above is expediently carried out in an inert organic solvent; for example in an aromatic hydrocarbon (e.g. benzene or toluene), a chlorinated hydrocarbon (e.g. chloroform), an ether (e.g. dioxane or dimethoxyethane), a lower alkanol (e.g. methanol or ethanol), a ketone (e.g. acetone or methyl ethyl ketone), dimethylformamide or dimethyl sulphoxide. It is preferred to carry out the reaction in the presence of an acid-binding agent, for example in the presence of an alkali metal carbonate (e.g. sodium or potassium carbonate) or in the presence of an inert organic base (e.g. triethylamine). An excess of the base of formula V can also be used as the acid-binding agent. The reaction is preferably carried out at a temperature between room temperature and the boiling point of the reaction mixture.

The reaction of a 10-oxo compound of formula VII with a compound of formula III in accordance with process embodiment (d) above leads to a corresponding enamine, i.e. a 10,11-unsaturated compound of formula I. This reaction is carried out, for example, in the presence of a strong acidic agent in an aromatic solvent with heating (e.g. to about 80° C to 150° C). As the acidic agent there can be used, for example, a mineral acid such as sulphuric acid or hydrochloric acid or a strong organic acid such as methanesulphonic acid or paratoluene-sulphonic acid. Benzene, toluene or o-, m- or p-xylene is preferably used as the aromatic solvent. During the heating an azeotrope is formed between the solvent and the water set free in the reaction, which can be distilled off. The water formed can also be removed by the addition of a water-withdrawing agent such as, for example, titanium tetrachloride.

A nitro group $R_1$ present in a compound of formula I can be reduced to the amino group in a manner known per se; for example, by catalytic hydrogenation in the presence of a noble metal catalyst (e.g. palladium/carbon), preferably in an inert organic solvent (e.g. a lower alkanol, ethyl acetate etc.) at a temperature between about 0° C and 50° C.

An amino group $R_1$ present in a compound of formula I can be converted into a di(lower alkyl)amino group by di(lower alkylation) in a manner known per se. For example, the di(lower alkylation) can be carried out using formaldehyde and an alkali metal cyanoborohydride (e.g. sodium cyanoborohydride), preferably in an inert organic solvent (e.g. acetonitrile) and at a temperature between room temperature and the boiling point of the mixture.

The compounds of formula I form salts with inorganic acids (e.g. hydrohalic acids such as hydrochloric acid, hydrobromic acid or hydroiodic acid, sulphuric acid, phosphoric acid or nitric acid) and with organic acids (e.g. tartaric acid, citric acid, camphorsulphonic acid, ethanesulphonic acid, toluenesulphonic acid, salicylic acid, ascorbic acid, maleic acid, mandelic acid etc.). The preferred salts are the hydrohalides, especially the hydrochloride, and the maleates. The acid addition salts are preferably manufactured in a suitable solvent (e.g. ethanol, acetone or acetonitrile) by treatment of the free base with the appropriate non-aqueous acid.

The compounds of formula I are partially crystalline solid substances which are relatively well soluble in dimethyl sulphoxide, dimethylformamide, chlorinated hydrocarbons (e.g. chloroform or methylene chloride) or alkanols (e.g. methanol or ethanol) and which are relatively insoluble in water.

The acid addition salts of the compounds of formula I are crystalline solid substances. They are well soluble in dimethyl sulphoxide and dimethylformamide and in alkanols (e.g. methanol or ethanol). They are partially soluble in chloroform, methylene chloride and water. They are relatively insoluble in benzene, ether and petroleum ether.

A cataleptic action ("wax rigidity", i.e. abnormally long retention of an enforced body position), when appearing upon administration of a central-depressant and/or neuroleptically active compound, is considered as a side-effect and is a sign of motoric disorders. The tricyclic compounds provided by the present invention have the advantage that they do not possess this disturbing side-effect or they have it only to a very slight extent. In order to demonstrate this, representative end products of the invention were administered intraperitonally to rats. The following products were investigated:

Product A: 3-[2-[4-(2-chloro-10,11-dihydro-dibenzo[b,f]thiepin-10-yl)-1-piperazinyl]-ethyl]-2-oxozolidinone maleate.

Product B: 3-[2-[4-(10,11-dihydro-2-methyl-dibenzo[b,f]thiepin-10-yl)-1-piperazinyl]-ethyl]-2-oxazolidinone maleate.

Chlorpromazine, a recognised central-depressant-/neuroleptic agent, was used as the standard.

The amimals are considered to be cataleptic when the homolateral extremities remain for at least 10 seconds in the crossed position. The number of cataleptic animals is noted every 30 minutes for 6 hours. The $ED_{50}$ is the dose at which 50% of the animals show catalepsy.

Results:

| Product | $ED_{50}$ mg/kg |
|---|---|
| A | >100 |
| B | 70 |
| Chlorpromazine | 6 |

The foregoing Table shows that no cataleptic action or only a slight cataleptic action exists with products A and B in comparison to chlorpromazine.

In order to demonstrate the central-depressant-/neuroleptic properties of the compounds of the invention, representative members thereof were subjected to the following tests:

I. Rotating rod test

In the rotating rod test, the ability of mice to achieve a coordinated, motoric performance is tested. After the peroral administration of the test substance, mice are placed on a horizontal, slowly rotating rod and the time until the mice fall off the rod is measured. The $ED_{50}$ is the dose which reduces the holding time to 50% with respect to the holding time before the administration of the test substance.

In this test, derivative A shows a strong action ($ED_{50}$ = 7.9 mg/kg) which is approximately equivalent to that of chlorpromazine ($ED_{50}$ = 5 mg/kg).

II. Determination of homovanillic acid

Rats are injected with the derivative to be tested 2 hours before they are killed.

Homovanillic acid is extracted from the supernatant of the brain homogenate into butyl acetate and later into an aqueous solution and oxidised with potassium ferricyanide to a fluorescent dimer. From the increased concentration of homovanillic acid (HVA) it can be concluded that the derivative under investigation acts like chlorpromazine, i.e. it increases the turnover of dopamine in the basal ganglia. The homovanillic acid titre in untreated rats is arbitrarily fixed at 100%.

| Product | Dose mg/kg p.o. | Increase of HVA, % |
|---|---|---|
| A | 50 | 340 |
| B | 50 | 255 |
| Chlorpromazine | 20 | 321 |

In this test, derivatives A and B show an activity which almost equalizes that of chlorpromazine.

III. Pole climbing test

This test gives information about behaviour reactions of rats. Rats are trained to avoid, by climbing up a vertical pole in the test chamber, an electrical impulse (unconditioned impulse) released via the wire-latticed floor some seconds after an acoustic signal (conditioned impulse).

The blocking of the conditioned reaction is determined by the parameter $ED_{50}$ (mg/kg p.o.); the blocking of the unconditioned reaction is determined by the parameter $ED_{10}$ (mg/kg p.o.).

The parameter $ED_{50}$ (blocking of the conditioned reaction) gives a measure of the neuroleptic activity strength of the test substance. The quotient $ED_{10}$ (blocking of the unconditioned reaction)/$ED_{50}$ (blocking of the conditioned reaction) gives a measure of the quality of action of the test substance, in that with increasing quotient a greater selectivity of the neuroleptic action (slighter neurotoxic side-effects) is present.

A comparison between product A and chlorpromazine shows the following result:

| Product | $ED_{50}$ (Blocking of the conditioned reaction) mg/kg p.o. | Quotient $ED_{10}$ (Blocking of the unconditioned reaction)/$ED_{50}$ (Blocking of the conditioned reaction) |
|---|---|---|
| A | 10 | 4.2 |
| Chlorpromazine | 11.6 | 3.5 |

In this test, product A not only shows a strong neuroleptic action but also a quality (selectivity) of the neuroleptic action, both of which somewhat exceed that of chlorpromazine.

The tricyclic compounds provided by the present invention can be used as medicaments; for example, in the form of pharmaceutical preparations which contain them in association with a compatible pharmaceutical carrier. This can be an organic or inorganic inert carrier material suitable for enteral (e.g. oral) or parenteral administration such as, for example, water, gelatine, lactose, starch, magnesium stearate, talc, vegetable oils, gum arabic, polyalkylene glycols, petroleum jelly etc. The pharmaceutical preparations can be made up in solid form (e.g. as tablets, dragees, suppositories or capsules) or in liquid form (e.g. as solutions, suspensions or emulsions). The pharmaceutical preparations may be sterilised and/or may contain adjuvants such as preservatives, stabilisers, wetting agents, emulsifiers, salts for the variation of the osmotic pressure or buffers. They can also contain other therapeutically valuable substances.

Expedient pharmaceutical dosage forms contain about 1 to 200 mg of a compound of formula I or of a salt thereof. Expedient oral dosage ranges lie at about 0.1 mg/kg per day to about 7.5 mg/kg per day. Expedient parenteral dosage ranges lie at about 0.01 mg/kg per day to about 0.75 mg/kg per day. However, the foregoing ranges can be varied upwards or downwards according to the individual requirements and the directions of the attending physician.

The following Examples illustrate the process provided by the present invention:

EXAMPLE 1

2.7 g of 1-(10,11-dihydro-2-methyl-dibenzo[b,f]thiepin-10-yl)-piperazine are treated, together with 4.3 g of powdered potassium carbonate, 200 mg of potassium iodide and 90 ml of toluene, with 3.2 g of N-(β-chloroethyl)-oxazolidinone and the mixture is heated for 24 hours under reflux. Then the mixture is poured on to ice-water, diluted with benzene and the organic phase washed with saturated soda solution and water, dried over sodium sulphate and concentrated under reduced pressure. There is obtained 3-[2-[4-(10,11-dihydro-2-methyl-dibenzo[b,f]thiepin-10-yl)-1-piperazinyl]-ethyl]-2-oxazolidinone which is recrystallised from acetone/petroleum ether. The maleate melts at 159°–161° C.

The 1-(10,11-dihydro-2-methyl-dibenzo[b,f]thiepin-10-yl)-piperazine used as starting material can be prepared as follows:

20 g of 5-methyl-anthranilic acid are suspended in 200 ml of 3-N hydrochloric acid at 0° C. There is added dropwise thereto with stirring a solution of 10 g of sodium nitrite and 20 ml of water and the mixture is stirred for 25 minutes at 0° C. A solution of 26.5 g of potassium iodide, 30 ml of 3-N hydrochloric acid and 30 ml of water is then added dropwise at 5°–10° C. The mixture is then stirred for a further 30 minutes at room temperature and for 2 hours under reflux. The mixture is then cooled, sodium thiosulphate is added until the solution is yellow (5 g) and the crystalline 2-iodo-5-methyl-benzoic acid obtained is filtered under suction and washed with water until neutral. The crude acid is dissolved in ether, washed well with sodium thiosulphate solution and water, dried over sodium sulphate and evaporated. There are obtained light-brown crystals of melting point 100°–112° C.

To a solution of 855 g of potassium hydroxide in 7 litres of water are added, at 50° C under argon, 420 g of thiophenol and the mixture is stirred for 15 minutes. There are then added thereto 22.1 g of copper powder and 1 kg of 2-iodo-5-methyl-benzoic acid and the mixture is heated for 7 hours under reflux. After cooling, the mixture is adjusted to pH 3 with 600 ml of concentrated hydrochloric acid and extracted with methylene chloride, washed with water, dried over sodium sulphate and concentrated to a thick crystal mash. This is filtered under suction, washed with cold ethanol and low-boiling petroleum ether and dried. There is obtained 3-methyl-6-(phenylthio)-benzoic acid of melting point 156°–157° C.

650 g of 3-methyl-6-(phenylthio)-benzoic acid in 7.5 litres of absolute methanol are slowly treated with 300 ml of concentrated sulphuric acid and the mixture is heated for 24 hours under reflux. The mixture is concentrated and the residue poured on to an ice-cold sodium bicarbonate solution. The mass is extracted with ether, washed with water, dried over sodium sulphate and concentrated. There is obtained methyl 3-methyl-6-(phenylthio)-benzoate as a red-brown oil which crystallises on standing.

322.5 g of methyl 3-methyl-6-(phenylthio)-benzoate in 3 litres of absolute tetrahydrofuran are treated dropwise over a period of 30 minutes under argon and under reflux with 420 ml of a 70% sodium-dihydrobis(2-methoxyethoxy)-aluminate solution in benzene and the mixture is boiled for a further 3 hours under reflux. Then the mixture is cooled to ca 4° C, diluted with 1 litre of benzene, hydrolysed with 700 ml of 2-N hydrochloric acid, then poured on to ice-water and treated with a further 400 ml of concentrated hydrochloric acid in order to obtain a clear solution. The organic phase is washed with water, dried over sodium sulphate, filtered and evaporated. There is obtained 3-methyl-6-(phenylthio)-benzyl alcohol as a red-brown oil.

570.7 g of 3-methyl-6-(phenylthio)-benzyl alcohol are dissolved in 1.5 litres of benzene and heated under reflux. There are added dropwise thereto within 45 minutes 352 ml of thionyl chloride and the mixture is boiled for a further 90 minutes. Then the mixture is concentrated under reduced pressure and there is obtained 3-methyl-6-(phenylthio)-benzyl chloride as a red-brown oil.

194 g of potassium cyanide in 250 ml of water are heated under reflux for 17 hours under an argon atmosphere with 616.9 g of 3-methyl-6-(phenylthio)-benzyl chloride in 900 ml of ethanol. Then the ethanol is distilled off under reduced pressure, the residue then diluted with water and extracted with ether. The extracts are washed with water, dried over sodium sulphate and evaporated. There is obtained 3-methyl-6-(phenylthio)-phenylacetonitrile as an oil.

500 g of 3-methyl-6-(phenylthio)-phenylacetonitrile, 1.2 litres of ethanol, 470 g of potassium hydroxide and 500 ml of water are heated for 12 hours under reflux. Then the ethanol is evaporated off under reduced pressure. The residue is treated with water until completely dissolved and the neutral constituents are extracted with benzene. The aqueous solution is filtered with the addition of some dicalite and active carbon, cooled and adjusted to pH 3 with concentrated hydrochloric acid. The mixture is then extracted three times with 1 litre of chloroform each time and the extracts are washed with water, dried over calcium chloride, filtered and concentrated under reduced pressure. The crude 3-methyl-6-(phenylthio)-phenylacetic acid obtained is recrystallised from benzene/hexane; melting point 132°–135° C.

192 g of polyphosphoric acid are heated under a nitrogen atmosphere to 100° C, quickly treated with 20 g of 3-methyl-6-(phenylthio)-phenylacetic acid and the mixture is stirred for 1 hour at 100°–103° C. Then the mixture is poured on to ice-water and extracted with ether. The extracts are washed successively with 2-N sodium hydroxide and water and dried over sodium sulphate. On concentration, the resulting 10,11-dihydro-2-methyl-dibenzo[b,f]thiepin-10-one begins to crystallise out. The crystallisation is completed by the addition of petroleum ether and cooling; melting point 83°–84° C.

10 g of 10,11-dihydro-2-methyl-dibenzo[b,f]thiepin-10-one are dissolved in 100 ml of dioxane and treated with 3.2 g of sodium borohydride in 5 ml of water. The mixture is subsequently stirred for 20 hours at room temperature. Then the mixture is concentrated under reduced pressure and the residue partitioned between ether and water. The ethereal solution is washed with saturated sodium chloride solution, dried over sodium sulphate and evaporated. There is obtained 10,11-dihydro-2-methyl-dibenzo[b,f]thiepin-10-ol as a colourless oil.

10 g of 10,11-dihydro-2-methyl-dibenzo[b,f]thiepin-10-ol, 100 ml of absolute benzene and 10 g of finely powdered calcium chloride are saturated at room temperature with dry hydrogen chloride gas (ca 2 hours) and then stirred for a further 20 hours. The calcium chloride is subsequently filtered off under a vacuum and washed with chloroform and the filtrate concentrated under reduced pressure. There is obtained 10-chloro-10,11-dihydro-methyl-dibenzo[b,f]thiepine as a yellow oil which crystallises on standing.

19.7 g of 10-chloro-10,11-dihydro-2-methyl-dibenzo-[b,f]thiepine dissolved in 100 ml of chloroform are heated under reflux for 24 hours together with 36.5 g of 1-carbethoxy-piperazine. Then the mixture is concentrated under reduced pressure and the residue crystallised from acetone/hexane. There is obtained 1-carbethoxy-4-(10,11-dihydro-2-methyl-dibenzo[b,f]thiepin-10-yl)-piperazine of melting point 96°–98° C.

5.4 g of 1-carbethoxy-4-(10,11-dihydro-2-methyl-dibenzo-[b,f]thiepin-10-yl)-piperazine, 80 ml of ethylene glycol, 4.64 g of potassium hydroxide and 0.33 ml of water and heated for 0.75 hour at 160° C. Then the mixture is poured on to water, extracted with ether, the extracts washed with saturated sodium chloride solution, dried over sodium sulphate and evaporated. There is obtained 1-(10,11-dihydro-2-methyl-dibenzo[b,f]thiepin-10-yl)-piperazine as an oil.

EXAMPLE 2

7.8 g of 1-(2-chloro-10,11-dihydro-dibenzo[b,f]thiepin-10-yl)-piperazine are treated, together with 11.6 g of powdered potassium carbonate, 0.2 g of potassium iodide and 100 ml of toluene, with 8.22 g of N-(β-chloroethyl)-oxazolidinone and the mixture is heated under reflux for 22 hours. Then the mixture is poured on to water and the organic phase washed with saturated soda solution and water, dried over sodium sulphate and concentrated under reduced pressure. There is obtained crude liquid 3-[2-[4-(2-chloro-10,11-dihydro-dibenzo[b,f]thiepin-10-yl)-1-piperazinyl]-ethyl]-2-oxazolidinone. The maleate is prepared by treatment with maleic acid in ethanol/ether; melting point 173°–175° C.

The 1-(2-chloro-10,11-dihydro-dibenzo[b,f]thiepin-10-yl)-piperazine used as starting material can be prepared as follows:

100 g of 2,10-dichloro-10,11-dihydro-dibenzo[b,f]-thiepin in 300 ml of chloroform are heated at reflux for 24 hours together with 182 g of 1-carbethoxy-piperazine. The mixture is then diluted with chloroform and water. The organic phase is washed several times with water and dried over magnesium sulphate. After filtration, the filtrate is concentrated under reduced pressure and the residue crystallised from acetone/hexane. There is obtained 1-carbethoxy-4-(2-chloro-10,11-dihydro-dibenzo[b,f]thiepin-10-yl)-piperazine of melting point 92°–93° C.

110 g of 1-carbethoxy-4-(2-chloro-10,11-dihydro-dibenzo[b,f]thiepin-10-yl)-piperazine, 1.5 litres of ethylene glycol, 104 g of potassium hydroxide and 5.4 ml of water are heated to 160° C for 1 hour. The mixture is then poured on to water and extracted with chloroform. The organic phase is washed with water, dried over magnesium sulphate and evaporated. There is obtained 1-(2-chloro-10,11-dihydro-dibenzo[b,f]thiepin-10-yl)-piperazine as an oil.

EXAMPLE 3

16.5 g of 1-(2-chloro-10,11-dihydro-dibenzo[b,f]-thiepin-10-yl)-piperazine are stirred, together with 9.8 g of 3-(3-chloro-propyl)-2-oxazolidinone, 5.25 g of sodium carbonate and 0.75 g of sodium iodide, in 100 ml of butanol for 15 hours at reflux temperature. The solvent is then evaporated off under reduced pressure and the residue is partitioned between chloroform and water. The organic phase is washed with water, dried over sodium sulphate and evaporated under reduced pressure. The residue is decolorised in methanol with active carbon. From the filtered solution there crystallises out upon cooling 3-[3-[4-(2-chloro-10,11-dihydro-dibenzo[b,f]thiepin-10-yl)-1-piperazinyl]-propyl]-2-oxazolidinone of melting point 136° C. The maleate prepared in acetone melts at 195°–196° C.

EXAMPLE 4

50 g of 10-chloro-10,11-dihydro-2-nitro-dibenzo[b,f]-thiepin and 140 g of 3-[2-(1-piperazinyl)-ethyl]-2-oxazolidione are held at 120° C for 15 minutes. After cooling, the mixture is diluted with 2-N sodium hydroxide and extracted with ethyl acetate. The organic phase is washed with water until neutral and then extracted with 2-N aqueous ethanesulphonic acid. The aqueous phase is extracted with ethyl acetate, then made alkaline and again extracted with ethyl acetate. The organic phase is washed with water until neutral, dried over magnesium sulphate and evaporated under reduced pressure. The resulting 3-[2-[4-(10,11-dihydro-2-nitro-dibenzo[b,f]thiepin-10-yl)-1-piperazinyl]-ethyl]-2-oxazolidinone is recrystallised from acetone; melting point 130°–132° C. The corresponding maleate of melting point 185°–187° C is obtained by reacting the base with maleic acid.

The 10-chloro-10,11-dihydro-2-nitro-dibenzo[b,f]-thiepin used as starting material can be prepared as follows:

A solution of 480 g of 2-chloro-5-nitro-benzaldehyde in 3.2 litres of ethanol is treated dropwise under a nitrogen atmosphere at 30°–40° C with stirring within 4 hours with a solution of 320 g of thiophenol in 120 g of sodium hydroxide, 2 litres of ethanol and 440 ml of water. The mixture is stirred for a further 30 minutes at 60° C, then cooled to 0° C and filtered. There is obtained crude crystalline 3-nitro-6-(phenylthio)-benzaldehyde of melting point 96°–100° C.

450 g of 3-nitro-6-(phenylthio)-benzaldehyde are suspended in 4 litres of ethanol and treated portionwise with 111 g of sodium borohydride. The mixture is stirred for a further 6 hours. The mixture is then diluted with 4 litres of water and extracted with ether. The organic solution is washed successively with water and aqueous sodium bicarbonate solution, dried over magnesium sulphate and evaporated under reduced pressure. The crude product is recrystallised from benzene/petroleum ether. There is obtained 3-nitro-6-(phenylthio)-benzyl alcohol of melting point 104°–107° C.

170.5 g of 3-nitro-6-(phenylthio)-benzyl alcohol are suspended in 54.5 ml of pyridine and 170 ml of chloroform and treated dropwise at a temperature below 20° C over a period of 30 minutes with a solution of 78 g of thionyl chloride in 55 ml of chloroform. The mixture is stirred for 30 minutes at 30° C and subsequently diluted with water. The organic phase is washed successively with water and aqueous sodium bicarbonate solution, dried over magnesium sulphate and concentrated. There is obtained crude 3-nitro-6-(phenylthio)-benzyl chloride of melting point 58°–60° C.

230 g of 3-nitro-6-(phenylthio)-benzyl chloride, 540 ml of ethanol and 320 ml of dioxane are treated with a solution of 70.5 g of potassium cyanide in 150 ml of water. The mixture is heated to reflux for 3 hours and subsequently concentrated under reduced pressure. The residue is diluted with water and extracted with benzene. The organic phase is washed with water and evaporated under reduced pressure. There is obtained 3-nitro-6-(phenylthio)-phenylacetonitrile as a brown oil.

210.3 g of 3-nitro-6-(phenylthio)-phenylacetonitrile, 210 ml of water, 210 ml of concentrated sulphuric acid and 210 ml of acetic acid are heated to reflux for 20 hours. The mixture is cooled and extracted with ether. The organic phase is washed successively with water and aqueous sodium carbonate solution. The aqueous phase is made acid with hydrochloric acid and extracted with ethyl acetate. The organic phase is washed with water, dried over magnesium sulphate, evaporated under reduced pressure and the residue recrystallised from benzene. There is obtained 3-nitro-6-(phenylthio)-phenylacetic acid of melting point 138°–140° C.

78.4 g of 3-nitro-6-(phenylthio)-phenylacetic acid and 400 g of polyphosphoric acid are held at 105°–110° C for 90 minutes with stirring. The mixture is subsequently diluted with ice and water and extracted with benzene. The organic phase is washed successively with water and aqueous sodium bicarbonate solution, dried over magnesium sulphate and evaporated under reduced pressure. There is obtained 10,11-dihydro-2-nitro-dibenzo[b,f]thiepin-10-one of melting point 171°–172° C.

165.3 g of 10,11-dihydro-2-nitro-dibenzo[b,f]thiepin-10-one are suspended in 6 litres of dioxane and treated with a solution of 63 g of sodium borohydride in 300 ml of dioxane and 300 ml of water. The mixture is stirred overnight at room temperature, then diluted with water, made neutral with sulphuric acid and extracted with ethyl acetate. The organic phase is washed with water, dried over sodium sulphate and evaporated under reduced pressure. The 10,11-dihydro-2-nitrodibenzo[b,f]thiepin-10-ol obtained is recrystallised from ethyl acetate; melting point 144°–146° C.

124 g of 10,11-dihydro-2-nitro-dibenzo[b,f]thiepin-10-ol are suspended in 69.5 ml of pyridine, 615 ml of benzene and 350 ml of chloroform and the mixture is treated dropwise with stirring at 0° C with 53 ml of thionyl chloride. The mixture is stirred overnight at room temperature and then for a further 30 minutes at 35°–40° C, cooled and diluted with water. The organic phase is washed successively with water and aqueous sodium bicarbonate solution, dired over magnesium sulphate and evaporated. There is obtained 10-chloro-10,11-dihydro-2-nitro-dibenzo[b,f]thiepin of melting point 74°–77° C.

The 3-[2-(1-piperazinyl)-ethyl]-2-oxazolidinone used as starting material can be prepared as follows:

744 g of 1-benzyl-piperazine are treated, together with 590 g of powdered potassium carbonate, 10 g of potassium iodide and 5 litres of toluene, with 450 g of 3-(2-chloroethyl)-2-oxazolidinone and the mixture is heated to reflux for 21 hours. The mixture is cooled, filtered and concentrated under reduced pressure. The residue is distilled under reduced pressure. There is obtained 3-[2-(4-benzyl-1-piperazinyl)-ethyl]-2-oxazolidinone which boils at 225°–235° C under a pressure of 2–2.5 mm. The compound is recrystallised from ethyl acetate; melting point 82°–84° C. The dihydrochloride of melting point 243°–245° C is obtained by treatment with an excess of hydrochloric acid in ethanol.

291 g of 3-[2-(4-benzyl-1-piperazinyl)-ethyl]-2-oxazolidinone dihydrochloride in 7 litres of methanol are hydrogenated in the presence of 70 g of palladium/carbon (5%) at 50° C and 10 atmospheres of hydrogen. The mixture is filtered and concentrated under reduced pressure. The residue is treated with sodium hydroxide, extracted with chloroform, filtered through diatomaceous earth and concentrated. There is obtained 3-[2-(1-piperazinyl)-ethyl]-2-oxazolidinone as a yellow oil. The dihydrochloride of melting point 203° C (decomposition) is obtained by treatment with an excess of hydrochloric acid in methanol/ether.

EXAMPLE 5

5.9 g of 1-(10,11-dihydro-2-iodo-dibenzo[b,f]thiepin-10-yl)-piperazine are treated, together with 3.3 g of powdered potassium carbonate, 0.07 g of potassium iodide and 40 ml of toluene, with 4.35 g of N-(β-chloroethyl)-oxazolidinone and the mixture is heated under reflux for 27 hours. The mixture is then poured on to water and diluted with chloroform. The organic phase is extracted with 2-N hydrochloric acid. The aqueous phase is made alkaline with sodium hydroxide and extracted with chloroform. The organic phase is dried over magnesium sulphate and concentrated under reduced pressure. The residue is chromatographed over aluminium oxide. There is obtained 3-[2-[4-(10,11-dihydro-2-iodo-dibenzo[b,f]thiepin-10-yl)-1-piperazinyl]-ethyl]-2-oxazolidinone which is converted into the maleate by treatment with maleic acid. The maleate melts at 176°–177° C.

The 1-(10,11-dihydro-2-iodo-dibenzo[b,f]thiepin-10-yl)-piperazine used as starting material can be prepared as follows:

88 g of 3-nitro-6-(phenylthio)-phenylacetic acid in 880 ml of ethyl acetate are hydrogenated at 40° C with hydrogen (10 atmospheres) and 9.5 g of palladium/carbon (5%). The mixture is filtered and the filtrate concentrated under reduced pressure. The resulting 3-amino-6-(phenylthio)-acetic acid is recrystallised from acetone/hexane and melts at 160°–162° C.

50 g of 3-amino-6-(phenylthio)-acetic acid and 500 g of polyphosphoric acid are held at 140° C for 10 minutes with stirring. The mixture is made neutral with sodium hydroxide and a large amount of water and then extracted with chloroform. The organic phase is washed with water, dried over magnesium sulphate and evaporated under reduced pressure. The resulting 2-amino-10,11-dihydro-dibenzo[b,f]thiepin-10-one is recrystallised from benzene; melting point 191°–193° C.

21.5 g of 2-amino-10,11-dihydro-dibenzo[b,f]thiepin-10-one are suspended at 5° C in 135 ml of water and 54.5 ml of concentrated hydrochloric acid. A solution of 9.1 g of sodium nitrite in 32 ml of water is then added dropwise and the mixture is stirred for 30 minutes at 5° C. The resulting diazonium salt solution is now added dropwise to a solution of 16.3 g of potassium iodide in 63 ml of water and 5.5 ml of concentrated sulphuric acid at 5° C over a period of 30 minutes. The mixture is stirred for a further 2 hours at room temperature and then at reflux until the iodine sublimation comes to an end. The mixture is then cooled and extrated with ethyl acetate. The organic solution is washed successively with sodium thiosulphate solution and water and dried over magnesium sulphate. The filtrate is evaporated and the residue chromatographed on silicagel. The resulting 10,11-dihydro-2-iodo-dibenzo[b,f]thiepin-10-one is recrystallised from acetone; melting point 129°–131° C.

12.0 g of 10,11-dihydro-2-iodo-dibenzo[b,f]thiepin-10-one are suspended in 100 ml of ethanol and the mixture is treated with 6 g of sodium borohydride. The mixture is stirred overnight, then treated with water and extracted with ether. The organic phase is washed with water until neutral, dried over magnesium sulphate and evaporated. The 10,11-dihydro-2-iodo-dibenzo[b,f]thiepin-10-ol obtained is recrystallised from ether; melting point 131°–133° C.

A solution of 10.3 g of 10,11-dihydro-2-iodo-dibenzo[b,f]thiepin-10-ol in 64 ml of benzene, 45 ml of chloroform and 6.3 ml of pyridine is treated dropwise at −5° C with 5.7 ml of thionyl chloride. The mixture is stirred for 90 minutes at room temperature and for 30 minutes at 35°–40° C and is subsequently treated with water. The organic phase is washed successively with aqueous sodium bicarbonate solution and water, dried over magnesium sulphate, filtered and concentrated. There is obtained 10-chloro-10,11-dihydro-2-iodo-dibenzo[b,f]thiepin as a brown oil.

10.1 g of 10-chloro-10,11-dihydro-2-iodo-dibenzo[b,f]thiepin and 23.3 g of piperazine are held at 120°–130° C for 1 hour. The mixture is cooled, diluted with 2-N sodium hydroxide and extracted with ether. The organic phase is washed with water until neutral and extracted with 500 ml of 2-N hydrochloric acid. The aqueous phase is made alkaline and extracted with chloroform. The organic phase is dried over magnesium sulphate and concentrated under reduced pressure. There is obtained 1-(10,11-dihydro-2-iodo-dibenzo[b,f]thiepin-10-yl)-piperazine as a brown oil.

EXAMPLE 6

12.5 g of 1-(2-bromo-10,11-dihydro-dibenzo[b,f]thiepin-10-yl)-piperazine are treated, together with 13 g of powdered potassium carbonate, 0.2 g of potassium iodide and 1 litre of toluene, with 13.2 g of N-(β-chloroethyl)-oxazolidinone and the mixture is heated under reflux for 25 hours. Then the mixture is poured on to ice-water and diluted with benzene. The benzene solution is washed neutral with water and extracted with 2-N hydrochloric acid. The aqueous phase is made alkaline with sodium hydroxide and extracted with benzene. The organic phase is washed with water, dried over magnesium sulphate and concentrated under reduced pressure. There is obtained crude 3-[ 2-[4-(2-bromo-10,11-dihydro-dibenzo[b,f]thiepin-10-yl)-1-piperazinyl]-ethyl ]-2-oxazolidinone which is converted into the maleate of melting point 170°–172° C by treatment with maleic acid.

The 1-(2-bromo-10,11-dihydro-dibenzo[b,f]thiepin-10-yl) -piperazine used as starting material can be prepared as follows:

A solution of 400 g of potassium hydroxide in 3 litres of water is treated at 45° C under a nitrogen atmosphere with 179 ml of thiophenol and the mixture is stirred for 15 minutes. After the addition of 7.1 g of copper powder and 564 g of 5-bromo-2-iodo-benzoic acid, the resulting mixture is heated under reflux for 5 hours and subsequently filtered while hot, acidified while cooling with 420 ml of concentrated hydrochloric acid and extracted with ethyl acetate. The organic solution is washed with water, dried over magnesium sulphate and evaporated under reduced pressure. There is obtained 3-bromo-6-(phenylthio)-benzoic acid of melting point 171°–173° C.

478 g of 3-bromo-6-(phenylthio)-benzoic acid in 1.5 litres of methanol and 200 ml of concentrated sulphuric acid are heated under reflux for 8 hours. The solution is concentrated under reduced pressure, treated with water and extracted with water. The organic solution is washed with aqueous sodium bicarbonate solution, dried over magnesium sulphate and concentrated under reduced pressure. There is obtained methyl 3-bromo-6-(phenylthio)-benzoate as a yellow oil.

A stirred solution of 65 g of lithium borohydride in 1 litre of tetrahydrofuran is treated dropwise under a nitrogen atmosphere over a period of 120 minutes with a solution of 483 g of methyl 3-bromo-6-(phenylthio)-benzoate in 1 litre of tetrahydrofuran. The mixture is stirred for a further 4 hours under reflux. The solution is cooled to 5° C and treated dropwise over a period of 3 hours with 700 ml of 3-N hydrochloric acid. After the addition of approximately 5 litres of water, the mixture is extracted with ether. The organic solution is washed with water and dried over magnesium sulphate. There is obtained crude 3-bromo-6-(phenylthio)-benzyl alcohol as a yellow oil.

445 g of 3-bromo-6-(phenylthio)-benzyl alcohol are dissolved in 800 ml of benzene and heated under reflux. 165 ml of thionyl chloride are added dropwise thereto and the mixture is boiled for a further 90 minutes. After evaporation of the solvent, there is obtained 3-bromo-6-(phenylthio)-benzyl chloride as a brown oil.

136.5 g of potassium cyanide in 183 ml of water are heated under reflux for 10 hours under a nitrogen atmosphere with 470 g of 3-bromo-6-(phenylthio)-benzyl chloride. The ethanol is distilled off under reduced pressure, the residue diluted with water and extracted with ether. The extracts are washed with water, dried over magnesium sulphate and evaporated. There is obtained 3-bromo-6-(phenylthio)-phenylacetonitrile as a brown oil.

442.6 g of 3-bromo-6-(phenylthio)-phenylacetonitrile, 775 ml of ethanol, 372 g of potassium hydroxide and 290 ml of water are heated under reflux for 8 hours. The ethanol is evaporated off under reduced pressure. The residue is treated with water until completely dissolved and the neutral constituents are extracted with toluene. The aqueous solution is cooled, acidified with concentrated hydrochloric acid and extracted with ethyl acetate. The organic phase is washed with water, dried over magnesium sulphate and concentrated under reduced pressure. The resulting crude 3-bromo-6-(phenylthio)-phenylacetic acid is recrystallised from benzene/hexane; melting point 118°–120° C.

2300 g of polyphosphoric acid are heated under a nitrogen atmosphere to 128° C, rapidly treated with 302 g of 3-bromo-6-(phenylthio)-phenylacetic acid and stirred at 120°–130° C for 8 minutes. After the addition of 1.5 kg of ice chips, the mixture is extracted with benzene. The organic solution is washed successively with water and aqueous sodium bicarbonate solution and then dried over magnesium sulphate. The resulting 2-bromo-10,11-dihydro-dibenzo[b,f]thiepin-10-one is distilled under reduced pressure; boiling point 170°–175° C/0.05 mm. The compound is recrystallised from acetone/hexane; melting point 143°–145° C.

50 g of 2-bromo-10,11-dihydro-dibenzo[b,f]thiepin-10-one are dispersed in 250 ml of ethanol, treated with 9.9 g of sodium borohydride and stirred for 1 hour. After the addition of water, the mixture is extracted with ether. The organic phase is washed with water, dried over magnesium sulphate and evaporated. There is obtained 2-bromo-10,11-dihydro-dibenzo[b,f]thiepin-10-ol of melting point 108°–110° C. 49.9 g of 2-bromo-10,11-dihydro-dibenzo[b,f]thiepin-10-ol, 250 ml of benzene and 18 g of finely powdered calcium chloride are saturated with hydrochloric acid gas at 15° C and then stirred for a further 3 hours at room temperature. The precipitate is filtered off and washed with benzene. The filtrate is concentrated under reduced pressure. There is obtained 2-bromo-10-chloro-10,11-dihydro-dibenzo[b,f]thiepin of melting point 122.5°–124° C.

32.5 g of 2-bromo-10-chloro-10,11-dihydro-dibenzo[b,f]thiepin in 120 ml of chloroform are heated under reflux for 24 hours together with 63.3 g of 1-carbethoxy-piperazine. The mixture is then poured on to ice-water and extracted with chloroform. The organic phase is dried over magnesium sulphate and concentrated under reduced pressure. There is obtained yellow, crude 1-carbethoxy-4-(2-bromo-10,11-dihydro-dibenzo[b,f]thiepin-10-yl)-piperazine. The hydrochloride of melting point 195° C is obtained by reacting the base with ethanolic hydrochloric acid.

47.2 g of 1-carbethoxy-4-(2-bromo-10,11-dihydro-dibenzo[b,f]thiepin-10-yl)-piperazine hydrochloride, 585 ml of ethylene glycol, 32.8 g of potassium hydroxide and 1.95 ml of water are heated to 160° C for 90 minutes. Then the mixture is poured on to water and extracted with chloroform. The organic solution is extracted with 2-N hydrochloric acid. The hydrochloric acid solution is made alkaline, extracted with chloroform, washed with water, dried over magnesium sulphate and concentrated under reduced pressure. There is obtained crystalline 1-(2-bromo-10,11-dihydro-dibenzo[b,f]thiepin-10-yl)-piperazine of melting point 112°–115° C.

EXAMPLE 7

9.4 g of 10-chloro-2-fluoro-10,11-dihydro-dibenzo[b,f]thiepin, 60 ml of chloroform and 17.1 g of 3-[2-(1-piperazinyl)-ethyl]-2-oxazolidinone are heated under reflux for 12 hours, then poured on to ice-water and extracted with chloroform/ether. The organic phase is extracted with 2-N hydrochloric acid. The aqueous phase is made alkaline with sodium hydroxide and extracted with benzene. The organic phase is washed with water and evaporated. There is obtained crude 3-[ 2-[4-(2-fluoro-10,11-dihydro-dibenzo[b,f]-thiepin-10-yl)-1-piperazinyl]-ethyl ]-2-oxazolidinone which melts at 158°–159° C after recrystallisation from ethyl acetate. This base is treated with maleic acid to give the maleate which melts at 199°–200° C.

The 10-chloro-2-fluoro-10,11-dihydro-dibenzo[b,f]thiepin used as starting material can be prepared as follows:

160 g of 5-fluoro-anthranilic acid hydrochloride are suspended in 768 ml of water and 76.8 ml of concentrated sulphuric acid at 0°–5° C. The suspension obtained is treated with stirring at 0°–5° C within the course of 30 minutes with a solution of 61.5 g of sodium nitrite in 153.5 ml of water. The diazonium salt solution obtained is stirred for a further 15 minutes and then treated dropwise at 0°–2° C with a solution of 193.5 g of potassium iodide in 41.5 ml of concentrated sulphuric acid and 400 ml of water. The mixture is stirred under reflux for 3 hours, then cooled and extracted with ethyl acetate. The organic phase is washed with aqueous sodium thiosulphate solution, dried over sodium sulphate and evaporated. There is obtained 5-fluoro-2-iodo-benzoic acid which melts at 142°–145° C.

A solution of 150 g of potassium hydroxide in 850 ml of water is treated with 47.5 ml of thiophenol at 55° C under a nitrogen atmosphere. The mixture is stirred for 15 minutes and subsequently treated with 1.9 g of copper powder and 207 g of 5-fluoro-2-iodo-benzoic acid. The mixture is heated under reflux for 7 hours, filtered while hot, cooled and acidified with concentrated hydrochloric acid. The precipitated product is filtered off, washed with water and dried. There is obtained 3-fluoro-6-(phenylthio)-benzoic acid which melts at 146°–148° C.

144 g of 3-fluoro-6-(phenylthio)-benzoic acid in 1000 ml of tetrahydrofuran is treated dropwise under a nitrogen atmosphere and under reflux with a 70% sodium-dihydro-bis(2-methoxyethoxy)-aluminate solution in benzene. The mixture is held under reflux for a further 2 hours. After the addition of 400 ml of benzene, the mixture is cooled to 20° C, acidified with 435 ml of 3-N hydrochloric acid and subsequently treated with 600 ml of concentrated hydrochloric acid. The organic phase is washed with water, dried over sodium sulphate and evaporated. There is obtained 3-fluoro-6-(phenylthio)-benzyl alcohol as a thick oil.

129 g of 3-fluoro-6-(phenylthio)-benzyl alcohol are dissolved in 385 ml of benzene and heated under reflux. 73 ml of thionyl chloride are added thereto and the resulting mixture is boiled for a further 30 minutes. The mixture is evaporated under reduced pressure. There is obtained 3-fluoro-6-(phenylthio)-benzyl chloride as a red-brown oil.

18.6 g of sodium cyanide in 222 ml of dimethyl sulphoxide are treated at 50° C with 74 g of 3-fluoro-6-(phenylthio)-benzyl chloride in 75 ml of dimethyl sulphoxide in one portion. The resulting dark solution is stirred at 45°–50° C for 1 hour, subsequently poured on to 1500 ml of ice-water and extracted with ether. The organic phase is washed three times with 500 ml of water each time, dried over sodium sulphate and evaporated. There is obtained 3-fluoro-6-(phenylthio)-phenylacetonitrile as a reddish oil.

80 g of 3-fluoro-6-(phenylthio)-phenylacetonitrile, 225 ml of ethanol, 75.5 g of potassium hydroxide and 225 ml of water are heated under reflux for 9 hours. The ethanol is subsequently evaporated off under reflux and the residue treated with water until completely dissolved, whereafter the neutral constituents are extracted with benzene. The aqueous solution is acidified with concentrated hydrochloric acid and extracted with chloroform. The organic phase is washed with water, dried over sodium sulphate and evaporated under reduced pressure. There is obtained 3-fluoro-6-(phenylthio)-phenylacetic acid which melts at 80°–83° C.

900 g of polyphosphoric acid are heated to 128° C under a nitrogen atmosphere, treated rapidly with 80 g of 3-fluoro-6-(phenylthio)-phenylacetic acid and stirred for 10 minutes at 120°–130° C (internal temperature). After the addition of ice chips, the mixture is extracted with benzene. The organic phase is washed successively with water, aqueous sodium carbonate solution and again with water, dried over sodium sulphate and evaporated. There is obtained 2-fluoro-10,11-dihydro-dibenzo[b,f]thiepin-10-one which boils at 118° C/0.07 mm and which melts at 98°–100° C.

22 g of 2-fluoro-10,11-dihydro-dibenzo[b,f]thiepin-10-one are suspended in 110 ml of ethanol and treated with 6.1 g of sodium borohydride. The mixture is heated under reflux for 10–15 minutes, then treated with water and extracted with chloroform. The organic phase is washed with water, dried over sodium sulphate and evaporated. There is obtained 2-fluoro-10,11-dihydro-dibenzo[b,f]thiepin-10-ol which melts at 110°–113° C.

21.2 g of 2-fluoro-10,11-dihydro-dibenzo[b,f]thiepin-10-ol, 110 ml of benzene and 7.9 g of finely powdered calcium chloride are saturated with hydrochloric acid gas at 15° C (2 hours). The precipitate is filtered off and washed with benzene. The filtrate is evaporated under reduced pressure. There is obtained 10-chloro-2-fluoro-10,11-dihydro-dibenzo[b,f]thiepin as pink crystals which melt at 90°–92° C.

EXAMPLE 8

24.1 g of 3-[ 2-[4-(10,11-dihydro-2-nitro-dibenzo[b,f]thiepin-10-yl)-1-piperazinyl]-ethyl ]-2-oxazolidinone in 2000 ml of ethyl acetate are hydrogenated in the presence of 5.7 g of palladium/carbon (5%) at 70° C and 10 atmospheres of hydrogen. After filtration, the filtrate is concentrated under reduced pressure. There is obtained 3-[ 2-[4-(2-amino-10,11-dihydro-dibenzo[b,f]thiepin-10-yl)-1-piperazinyl]-ethyl ]-2-oxazolidinone which melts at 193°–196° C. After chromatographic purification over aluminium oxide using acetone/hexane as the elution agent, there is obtained a pure product which melts at 195.5°–196.5° C.

EXAMPLE 9

7 g of 3-[ 2-[4-(2-amino-10,11-dihydro-dibenzo[b,f]thiepin-10-yl)-1-piperazinyl]-ethyl ]-2-oxazolidinone, 13.1 ml of 40% formaldehyde and 61 ml of acetonitrile are treated with 3.32 g of sodium cyanoborohydride and the resulting mixture is treated dropwise over a period of 10 minutes with 1.5 ml of acetic acid. The mixture is stirred for a further 90 minutes, treated dropwise with a further 1.5 ml of acetic acid and again stirred for 15 minutes. The mixture is now extracted with 200 ml of ether and the organic phase washed three times with 1-N aqueous potassium hydroxide solution, dried over sodium sulphate and evaporated. There is obtained 3-[ 2-[4-(10,11-dihydro-2-dimethylamino-dibenzo[b,f]thiepin-10-yl)-1-piperazinyl]-ethyl ]-2-oxazolidinone which melts at 168°–170° C. After recrystallisation from ethanol, this compound melts at 171°–173° C. By treatment with maleic acid there is obtained the corresponding maleate which melts at 143.5°–144.5° C after recrystallisation from acetonitrile.

EXAMPLE 10

8.3 g of 1-(2-chloro-10,11-dihydro-dibenzo[b,f]thiepin-10-yl)-piperazine are treated, together with 11.6 g of powdered potassium carbonate, 0.2 g of potassium iodide and 80 ml of toluene, with 8.6 g of β-chloroethyl-3-methyl-2-imidazolidinone and the mixture is heated under reflux for 20 hours. The mixture is then poured into water, the organic phase washed with water, dried over sodium sulphate and evaporated. There is obtained 1-[ 2-[4-(2-chloro-10,11-dihydro-dibenzo[b,f]thiepin-10-yl)-1-piperazinyl]-ethyl ]-3-methyl-2-imidazolidinone as a brown oil. By treatment of this compound with maleic acid in ethanol/ether there is obtained the corresponding maleate which melts at 186°–188° C.

EXAMPLE 11

11.9 g of 10-chloro-10,11-dihydro-2-dimethylsulphamoyldibenzo[b,f]thiepin in 250 ml of chloroform are treated with 20 g of 3-[2-(1-piperazinyl)-ethyl]-2-oxazolidinone and the mixture is heated under reflux for 24 hours. Then the mixture is evaporated under reduced pressure and the residue taken up in ethyl acetate. The organic phase is washed with water, dried over magnesium sulphate and evaporated under reduced pressure. The residue is dissolved in benzene and filtered through a column filled with 100 g of aluminium oxide (activity stage II). The eluate is evaporated and, for the purpose of further purification, chromatographed on 75 g of silicagel (0.2–0.5 mm), elution being effected with a 1:1 mixture of chloroform saturated with concentrated ammonia/carbon tetrachloride. The purified product is recrystallised from ethyl acetate/petroleum ether. There is obtained 3-[2-[4-{10,11-dihydro-2-dimethylsulphamoyl-dibenzo[b,f]-thiepin-10-yl}-1-piperazinyl]-ethyl]-2-oxazolidinone which melts at 164°–165° C.

The 10-chloro-10,11-dihydro-2-dimethylsulphamoyl-dibenzo[b,f]thiepin used as starting material can be prepared as follows:

22.9 g of 2-amino-10,11-dihydro-dibenzo[b,f]thiepin-10-one are suspended in 50 ml of concentrated hydrochloric acid and treated dropwise at 0° C within 30 minutes with 8.6 g of sodium nitrite in 20 ml of water. The resulting suspension is stirred at 0° C for 3–4 hours. The still undissolved constituents are removed by filtration and the cold filtrate is immediately added to a solution, cooled to 10°–20° C, of 73 g of sulphur dioxide in 150 ml of glacial acetic acid containing 7.6 g of cupric chloride and 50 ml of benzene. The resulting mixture is heated to 40°–45° C for 5–10 minutes and subsequently stirred at 20° C for 3 hours. The mixture is then poured on to ice-water and extracted with benzene. The organic phase is washed with water, dried over magnesium sulphate, filtered and evaporated. The residue is dissolved in dioxane, treated with 50 mg of dimethylamine and left to stand at room temperature for 15 hours. The mixture is evaporated under reduced pressure. For the purpose of purification, the residue is dissolved in benzene and chromatographed on silicagel (particle size 0.2–0.5 mm) using chloroform as the elution agent. There is obtained 10,11-dihydro-2-dimethylsulphamoyl-dibenzo[b,f]thiepin-10-one, the IR spectrum of which agrees with the structure.

14 g of 10,11-dihydro-2-dimethylsulphamoyl-dibenzo[b,f]-thiepin-10-one in 200 ml of dioxane are treated with 3.5 g of sodium borohydride in 15 ml of water and the mixture is stirred at 40° C for 4 hours. The mixture is evaporated under reduced pressure and the residue taken up in ethyl acetate and water. The organic phase is washed with water, dried and evaporated. 10,11-dihydro-2-dimethylsulphamoyl-dibenzo[b,f]-thiepin-10-ol is obtained.

Hydrochloric acid gas is introduced at 10° C for 2 hours into a mixture of 12 g of 10,11-dihydro-2-dimethylsulphamoyl-dibenzo[b,f]thiepin-10-ol, 250 ml of benzene and 20 g of calcium chloride. The mixture is then left to stand at room temperature for 20 hours. The excess hydrochloric acid is driven off by the introduction of nitrogen. The mixture is filtered and evaporated under reduced pressure. 10-chloro-10,11-dihydro-2-dimethylsulphamoyl-dibenzo[b,f]thiepin is obtained.

EXAMPLE 12

The following compounds are prepared in a manner analogous to that described in Example 3: from 1-(2-chloro-10,11-dihydro-dibenzo[b,f]thiepin-10-yl)-piperazine and 1-(2-chloroethyl)-2-pyrrolidinone there is obtained 1-[2-[4-(2-chloro-10,11-dihydro-dibenzo[b,f]thiepin-10-yl)-1-piperazinyl]-ethyl]-2-pyrrolidinone. The corresponding maleate is prepared in acetone and is recrystallised from water; melting point 179°–180° C.
from
1-(10,11-dihydro-2-methyl-dibenzo[b,f]thiepin-10-yl)-piperazine and 3-(3-chloropropyl)-2-oxazolidinone there is obtained 3-[3-[4-(10,11-dihydro-2-methyl-dibenzo[b,f]thiepin-10-yl)-1-piperazinyl]-propyl]-2-oxazolidinone; melting point 144°–145° C. The dimaleate prepared in acetone melts at 140°–142° C.
from
1-(2-chloro-10,11-dihydro-dibenzo[b,f]thiepin-10-yl)-piperazine and 1-(2-chloroethyl)-2-benzimidazolinone there is obtained 1-[2-[4-(2-chloro-10,11-dihydro-dibenzo[b,f]thiepin-10-yl)-1-piperazinyl]-ethyl]-2-benzimidazolinone; melting point 161°–164° C. The bis(methanesulphonate) prepared in methanol and ether melts at 160°–165° C (decomposition).
from
1-(2-chloro-10,11-dihydro-dibenzo[b,f]thiepin-10-yl)-piperazine and 1-(2-chloroethyl)-2-piperidone there is obtained 1-[2-[4-(2-chloro-10,11-dihydro-dibenzo-[b,f]thiepin-10-yl)-1-piperazinyl[-ethyl]-2-piperidone; melting point 133° C. The bis(methanesulphonate) prepared in ethanol melts at 156°–159° C (decomposition).
from
1-(10,11-dihydro-2-methyl-dibenzo[b,f]thiepin-10-yl)-piperazine and 1-(2-chloroethyl)-2-pyrrolidinone there is obtained 1-[2-[4-(10,11-dihydro-2-methyl-dibenzo-[b,f]thiepin-10-yl)-1-piperazinyl]-ethyl]-2-pyrrolidinone. The corresponding maleate melts at 142°–144° C.

EXAMPLE 13

17 g of 10-chloro-10,11-dihydro-2-trifluoromethyl-dibenzo[b,f]thiepin in 90 ml of chloroform and 26.2 g of 3-[2-(1-piperazinyl)-ethyl]-2-oxazolidinone are heated under reflux for 14 hours. The mixture is evaporated and the residue treated with ice-water, ether and 2-N aqueous sodium hydroxide. After equilibration, the organic phase is washed with water and acidified with ethanolic hydrochloric acid. The precipitate which separates is filtered off and dissolved in about 400 ml of water. The aqueous solution is extracted with ether. The aqueous solution is treated with ice, made alkaline with aqueous sodium hydroxide solution and extracted with about 350 ml of benzene. The benzene phase is dried over sodium sulphate, filtered and evaporated. There is obtained 3-[2-[4-(10,11-dihydro-2-trifluoromethyl-dibenzo[b,f]thiepin-10-yl)-1-piperazinyl]-ethyl]-2-oxazolidinone as an oil. By treatment with maleic acid there is obtained the corresponding maleate which is crystallised from ethanol/ether; melting point 168°–169° C.

The 10-chloro-10,11-dihydro-2-trifluoromethyl-dibenzo[b,f]thiepin used as starting material can be prepared as follows:

A solution of 6.5 g of potassium hydroxide in 80 ml of water is treated under a nitrogen atmosphere at 50° C with 10.3 ml of thiophenol and the mixture is then stirred for 30 minutes. After the addition of 0.5 g of copper powder and 22.5 g of 4-chloro-3-nitro-benzotrifluoride in 100 ml of ethanol, the mixture is heated under reflux for 48 hours. After filtration, the mixture is poured into water and extracted with ether. The ethereal phase is washed successively with aqueous sodium carbonate solution, water, aqueous sodium chloride solution, 2-N aqueous hydrochloric acid and water, dried, filtered and evaporated. There is obtained 3-nitro-4-(phenylthio)-benzotrifluoride as a red oil.

26.9 g of 3-nitro-4-(phenylthio)-benzotrifluoride in 250 ml of ethanol are hydrogenated in the presence of 10 g of Raney-nickel at room temperature and atmospheric pressure for 17 hours. The mixture is filtered and evaporated under reduced pressure. There is obtained 3-amino-4-(phenylthio)-benzotrifluoride as a red-brown oil. The compound is distilled under greatly reduced pressure and boils at 110°–135° C/0.1 mm; orange-coloured oil.

36 g of 3-amino-4-(phenylthio)-benzotrifluoride, 70 ml of water and 21 ml of methanesulphonic acid are heated to 90° C, stirred at this temperature for 20 minutes and subsequently cooled to 0° C. The suspension obtained is treated dropwise over a period of 15 minutes at 0° C with a solution of 9.25 g of sodium nitrite in 33 ml of water, care being taken to ensure that the temperature does not rise above 10° C. The mixture is stirred for about 1 hour at 0° C, filtered and added over a period of about 45 minutes to a suspension of copper cyanide pre-warmed to 100° C (prepared by the addition of 33.75 g of copper sulphate to 37 g of potassium cyanide in 165 ml of water). The dark solution obtained is stirred at 100° C for 1 hour, cooled, treated with 350 ml of benzene and stirred overnight. The mixture is filtered through diatomaceous earth and the filter cake washed with benzene. The organic phase is washed twice with 150 ml of saturated sodium chloride solution each time, dried over sodium sulphate, filtered and evaporated. There is obtained 2-(phenylthio)-5-trifluoromethyl-benzonitrile as a dark oil.

6 g of 2-(phenylthio)-5-trifluoromethyl-benzonitrile, 40 ml of 15% aqueous sodium hydroxide solution and 12 ml of ethanol are heated under reflux for 12 hours and then cooled. After the addition of 100 ml of water, the mixture is extracted with 80 ml of benzene. The aqueous phase is cooled to 0° C and acidified with concentrated hydrochloric acid. The precipitate which separates out is extracted with methylene chloride. The organic phase is washed with water until neutral, dried over sodium sulphate, filtered and evaporated. There is obtained 2-(phenylthio)-5-trifluoromethyl-benzoic acid which melts at 140°–145° C.

100 g of 2-(phenylthio)-5-trifluoromethyl-benzoic acid, 750 ml of absolute methanol and 100 ml of sulphuric acid are heated under reflux for 24 hours. The solution is concentrated under reduced pressure and treated with water and benzene. After equilibration, the organic phase is washed successively with saturated aqueous sodium chloride solution, saturated aqueous sodium bicarbonate solution and saturated aqueous sodium chloride solution. The benzene phase is subsequently dried over sodium sulphate, filtered and evaporated. There is obtained methyl 2-(phenylthio)-5-trifluoromethyl-benzoate as a yellow oil.

21.5 g of lithium borohydride are suspended in 375 ml of tetrahydrofuran under a nitrogen atmosphere and heated to reflux. This suspension is treated dropwise under reflux over a period of 20 minutes with a solution of 130 g of methyl 2-(phenylthio)-5-trifluoromethyl-benzoate in 600 ml of tetrahydrofuran. The mixture is stirred under reflux for 2 hours and subsequently cooled to 2° C. The mixture is treated over a period of 10 minutes with 450 ml of 2-N aqueous hydrochloric acid in such a manner that the temperature does not exceed 10° C. After the addition of 750 ml of water, the mixture is extracted with 1000 ml of ether. The organic phase is washed twice with 300 ml of water each time, dried over sodium sulphate, filtered and evaporated. There is obtained 2-(phenylthio)-5-trifluoromethyl-benzyl alcohol as a light-yellow oil which crystallises spontaneously; melting point 84° C.

96 g of 2-(phenylthio)-5-trifluoromethyl-benzyl alcohol are dissolved in 450 ml of absolute benzene and heated to reflux. The solution thus obtained is treated dropwise over a period of 20 minutes with 48 ml of thionyl chloride and the mixture is subsequently stirred at reflux for 30 minutes. After cooling, the mixture is evaporated under reduced pressure. There is obtained 2-(phenylthio)-5-trifluoromethyl-benzyl chloride as a brown-yellow oil.

11.2 g of sodium cyanide in 135 ml of dimethyl sulphoxide are warmed to 40° C and treated dropwise over a period of 10 minutes with a solution of 87 g of 2-(phenylthio)-5-trifluoromethyl-benzyl chloride in 72 ml of dimethyl sulphoxide. The mixture is stirred at 40° C for 9 hours, cooled to room temperature, treated with 200 ml of water and extracted with 200 ml of ether. The aqueous phase is then extracted twice with 100 ml of ether each time. The combined organic phases are now washed twice with 200 ml of water each time, dried over sodium sulphate and evaporated under reduced pressure. There is obtained 2-(phenylthio)-5-trifluoromethyl-phenylacetonitrile as a dark-red oil.

15 g of 2-phenylthio-5-trifluoromethyl-phenylacetonitrile, 15.1 g of sodium hydroxide, 90 ml of water and 23 ml of ethanol are heated under reflux for 12 hours and subsequently concentrated. After the addition of 200 ml of water, the residue is extracted with 100 ml of benzene. The aqueous phase is back-extracted with 50 ml of benzene. The combined organic phases are extracted with 0.5-N aqueous sodium hydroxide solution. The aqueous phase is acidified with hydrochloric acid and extracted with 150 ml of chloroform. The organic phase is washed with aqueous sodium chloride solution, dried and evaporated. There is obtained 2-(phenylthio)-5-trifluoromethyl-phenylacetic acid in the form of crystals which melt at 102°–103° C.

217 g of polyphosphoric acid are heated under a nitrogen atmosphere to 110° C, treated with 21 g of 2-(phenylthio)-5-trifluoromethyl-phenylacetic acid and stirred at 100°–110° C for 8 minutes. The mixture is then cooled and treated with 100 g of ice and 250 ml of ice-water. The mixture is then extracted with 300 ml of benzene. The organic phase is washed successively with two 150 ml portions of water, two 200 ml portions of saturated aqueous sodium carbonate solution and 150 ml of aqueous sodium chloride solution, dried over sodium sulphate, filtered and evaporated under reduced pressure. There is obtained 10,11-dihydro-2-trifluoromethyl-dibenzo[b,f]thiepin-10-one in the form of light-yellow crystals which melt at 103°–104° C.

12 g of 10,11-dihydro-2-trifluoromethyl-dibenzo[b,f]thiepin-10-one are dissolved in 110 ml of absolute ethanol and treated with 4 g of sodium borohydride. The mixture is held at reflux for 12 minutes, cooled to 30° C and treated with 350 ml of water and 100 ml of chloroform. After equilibration, the organic phase is washed with aqueous sodium chloride solution, dried over sodium sulphate and evaporated under reduced pressure. There is obtained 10,11-dihydro-2-trifluoromethyl-dibenzo[b,f]thiepin-10-ol in the form of yellow crystals which melt at 122°–123° C.

11.4 g of 10,11-dihydro-2-trifluoromethyl-dibenzo[b,f]thiepin-10-ol, 100 ml of benzene and 4 g of calcium chloride are saturated with hydrochloric acid gas for 2 hours at 15° C and subsequently stirred at room temperature for 3 hours. The mixture is filtered and concentrated under reduced pressure. There is obtained 10-chloro-10,11-dihydro-2-trifluoromethyl-dibenzo[b,f]thiepin in the form of yellow crystals.

EXAMPLE 14

8.5 g of 2-chloro-10,11-dihydro-dibenzo[b,f]thiepin-10-one, 30 g of 3-[2-(1-piperazinyl)-ethyl]-2-oxazolidinone and 100 ml of benzene are treated dropwise under an argon atmosphere at 20° C with 5.2 g of titanium tetrachloride in 25 ml of benzene. The mixture is heated under reflux for 20 hours and subsequently poured on to a mixture of ice and aqueous sodium bicarbonate solution. The mixture is stirred for 1 hour and filtered through diatomaceous earth. The aqueous phase is separated and washed successively with benzene and chloroform. The organic phases are combined and washed successively with aqueous sodium chloride solution and water, dried, filtered and evaporated under reduced pressure. There is obtained 3-[2-[4-(2-chloro-dibenzo[b,f]thiepin-10-yl)-1-piperazinyl]-ethyl]-2-oxazolidinone as a red-brown viscous oil which, for the purpose of purification, is chromatographed on 100 g of silica dioxide [elution agent ethanol: methanol: concentrated ammonia (100:50:10)]. There is obtained a red-brown oil which is crystallised from acetone with the aid of active carbon. There are obtained beige-coloured crystals which are converted into the corresponding maleate (beige-coloured crystals) of melting point 232°–233° C (decomposition) by treatment with maleic acid in acetone.

EXAMPLE 15

750 mg of 3-[2-[4-(2-chloro-dibenzo[b,f]thiepin-10-yl)-1-piperazinyl]-ethyl]-2-oxazolidinone, 0.6 g of sodium borohydride and 30 ml of diglyme are treated dropwise under an argon atmosphere at 20°–30° C over a period of 15 minutes with 2.7 g of oxalic acid dihydrate in 15 ml of diglyme. The mixture is heated for 4 hours at an internal temperature of 100° C and subsequently evaporated under reduced pressure. The residue is treated with chloroform and 2-N sodium hydroxide solution. After equilibration, the aqueous phase is separated and washed twice with chloroform. The combined chloroform extracts are washed with water, dried over potassium carbonate and active carbon, filtered and evaporated under reduced pressure. There is obtained 3-[2-[4-(2-chloro-10,11-dihydro-dibenzo[b,f]-thiepin-10-yl)-1-piperazinyl]-ethyl]-2-oxazolidinone in the form of a brown oil. The maleate of melting point 173°–175° C is prepared by treatment with maleic acid in ethanol/ether.

The following Example illustrates a typical pharmaceutical preparation containing the dibenzo[b,f]thiepin derivatives provided by the invention:

EXAMPLE

Tablets of the following composition are produced:

| | |
|---|---:|
| 3-[2-[4-(2-chloro-10,11-dihydro-dibenzo-[b,f]thiepin-10-yl)-1-piperazinyl]-ethyl]-2-oxazolidinone maleate | 28.27 g |
| Lactose | 110.00 g |
| Maize starch | 57.73 g |
| Talc | 3.40 g |
| Magnesium stearate | 0.60 g |
| | 200.00 g |

The ingredients are intimately mixed with one another and pressed to tablets each weighing 200 mg. The tablets are subsequently covered with ethylcellulose and Carbowax.

We claim:

1. A compound of the formula

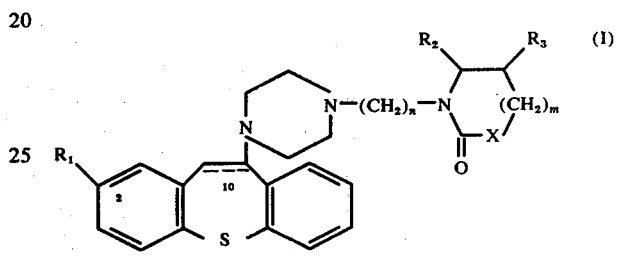

wherein n is 2 or 3, $R_1$ is halogen, lower alkyl, di(lower alkyl)sulphamoyl, nitro, amino, di(lower alkyl)-amino or trifluoromethyl, X is methylene, m is zero and $R_2$ and $R_3$ each is hydrogen, or a pharmaceutically acceptable acid addition salt thereof.

2. A compound in accordance with claim 1, 1-{2-[4-(10,11-dihydro-2-methyl-dibenzo[b,f]thiepin-10-yl)-1-piperazinyl]-ethyl}-2-pyrrolidinone, or a pharmaceutically acceptable acid addition salt thereof.

3. A compound in accordance with claim 1, 1-{2-[4-(2-chloro-10,11-dihydro-dibenzo[b,f]thiepin-10-yl)-1-piperazinyl]-ethyl}-2-pyrrolidinone, or a pharmaceutically acceptable acid addition salt thereof.

* * * * *

UNITED STATES PATENT OFFICE
CERTIFICATE OF CORRECTION

Patent No. 4,006,144  Dated February 1, 1977

Inventor(s) Max Gerecke et al.  Page 1 of 2

It is certified that error appears in the above-identified patent and that said Letters Patent are hereby corrected as shown below:

Cover Sheet "[30] Foreign Application Priority Data"
    July 21, 1972    Switzerland    1001/72    should be:

July 21, 1972    Switzerland    11001/72

UNITED STATES PATENT OFFICE
CERTIFICATE OF CORRECTION

Patent No. 4,006,144  Dated February 1, 1977

Inventor(s) Max Gerecke et al.   Page 2 of 2

It is certified that error appears in the above-identified patent and that said Letters Patent are hereby corrected as shown below:

Column 26, claim 1, lines 20-30

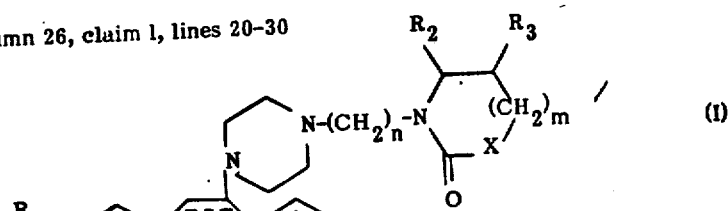

should be:

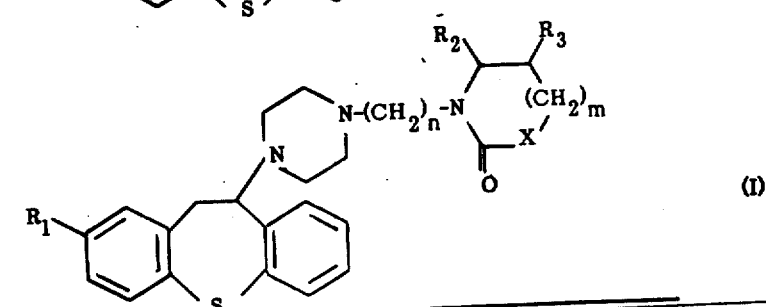

Signed and Sealed this sixteenth Day of August 1977

[SEAL]

Attest:

RUTH C. MASON
Attesting Officer

C. MARSHALL DANN
Commissioner of Patents and Trademarks